US005737058A

United States Patent [19]

Umemura et al.

[11] Patent Number: 5,737,058

[45] Date of Patent: Apr. 7, 1998

[54] EYE EXAMINATION APPARATUS USING ULTRASONIC WAVE RADIATION

[75] Inventors: Izumi Umemura, Hiratsuka; Nobuyuki Miyake, Yokohama; Seiho Yamashita; Yoichi Iki, both of Kawasaki, all of Japan

[73] Assignee: Nikon Corporation, Tokyo, Japan

[21] Appl. No.: 589,632

[22] Filed: Jan. 22, 1996

[30] Foreign Application Priority Data

Jan. 23, 1995 [JP] Japan .................................... 7-008377
Aug. 17, 1995 [JP] Japan .................................... 7-209807

[51] Int. Cl.$^6$ ................................ A61B 3/14; A61B 3/10

[52] U.S. Cl. ........................... 351/208; 351/211; 351/221

[58] Field of Search .................................... 351/200, 205, 351/211, 212, 208, 221

[56] References Cited

U.S. PATENT DOCUMENTS 5,561,482 10/1996 Miyake .................................. 351/208

FOREIGN PATENT DOCUMENTS 4-73046 3/1992 Japan .
6-237897 8/1994 Japan .................................... 351/221

*Primary Examiner*—Huy Mai
*Attorney, Agent, or Firm*—Shapiro and Shapiro

[57] ABSTRACT

An eye examination apparatus comprises an ultrasonic transmitter for transmitting ultrasonic wave radiation to an area around an eye to be examined, an ultrasonic receiver for receiving the reflected wave radiation of the ultrasonic wave radiation, and a judging device for judging whether the eye to be examined is the right eye or the left eye based on the result of the reception by the ultrasonic receiver.

4 Claims, 8 Drawing Sheets

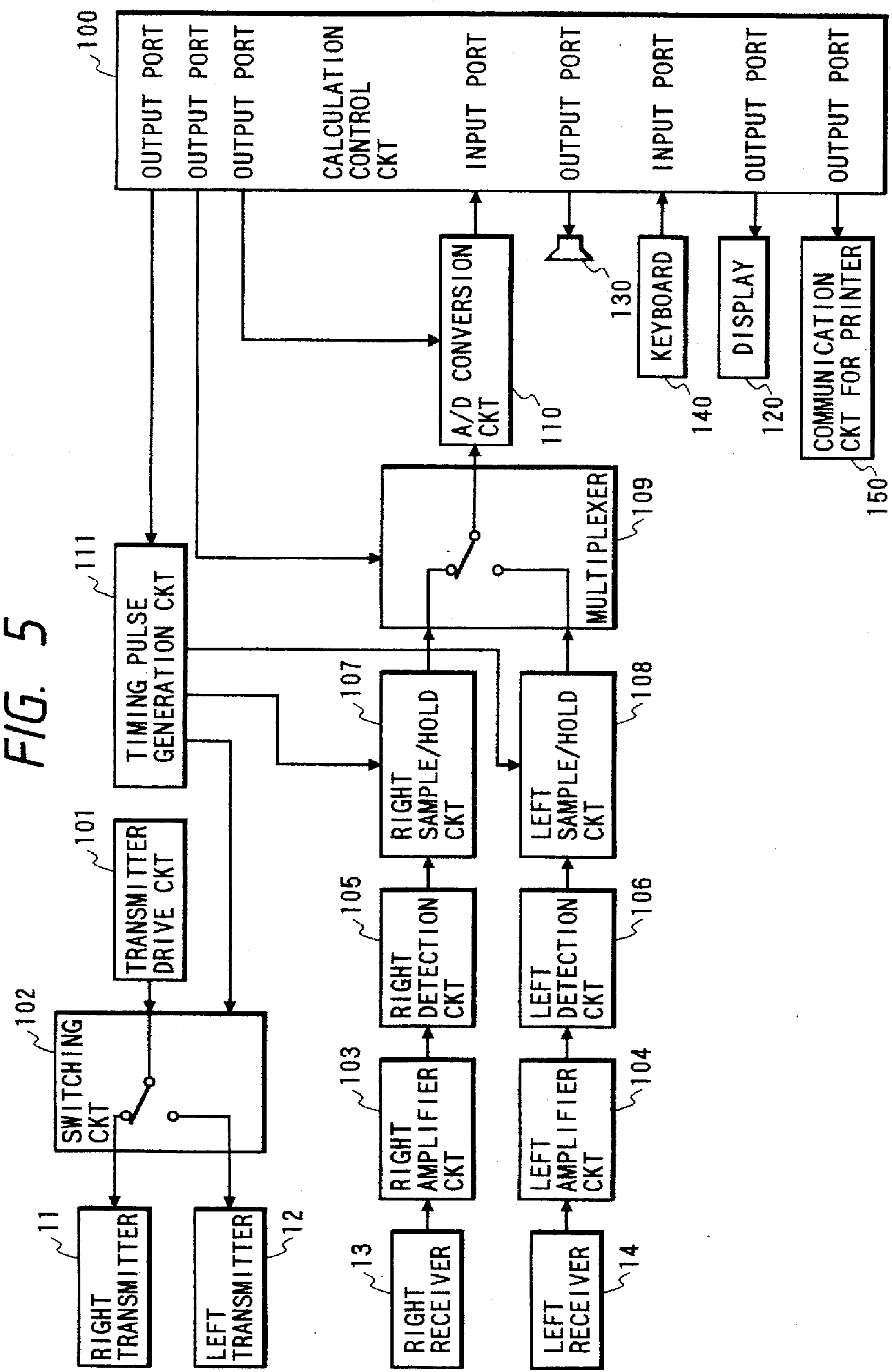
FIG. 5
100
OUTPUT PORT
OUTPUT PORT
OUTPUT PORT
CALCULATION CONTROL CKT
INPUT PORT
OUTPUT PORT
INPUT PORT
OUTPUT PORT
OUTPUT PORT
A/D CONVERSION CKT
110
130
KEYBOARD
140
DISPLAY
120
COMMUNICATION CKT FOR PRINTER
150
TIMING PULSE GENERATION CKT
111
MULTIPLEXER
109
TRANSMITTER DRIVE CKT
101
SWITCHING CKT
102
RIGHT SAMPLE/HOLD CKT
107
LEFT SAMPLE/HOLD CKT
108
RIGHT DETECTION CKT
105
LEFT DETECTION CKT
106
RIGHT AMPLIFIER CKT
103
LEFT AMPLIFIER CKT
104
RIGHT TRANSMITTER
11
LEFT TRANSMITTER
12
RIGHT RECEIVER
13
LEFT RECEIVER
14

FIG. 8A TRANSMITTER DRIVE CIRCUIT OUTPUT
FIG. 8B LEFT TRANSMITTER DRIVE SIGNAL
FIG. 8C RIGHT TRANSMITTER DRIVE SIGNAL
FIG. 8D LEFT RECEIVER OUTPUT
FIG. 8E RIGHT RECEIVER OUTPUT
FIG. 8F LEFT DETECTION CIRCUIT OUTPUT
FIG. 8G RIGHT DETECTION CIRCUIT OUTPUT
FIG. 8H LEFT SAMPLE/ HOLD CIRCUIT OUTPUT
FIG. 8I RIGHT SAMPLE/ HOLD CIRCUIT OUTPUT
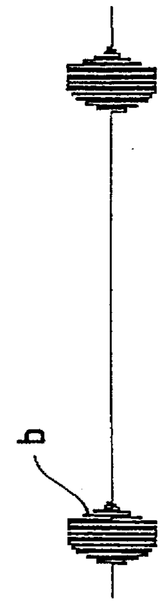
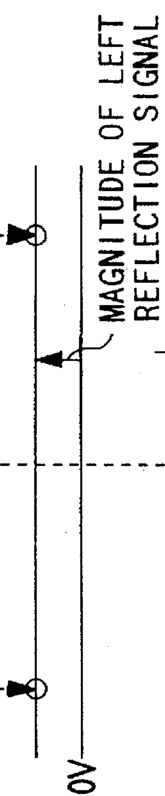
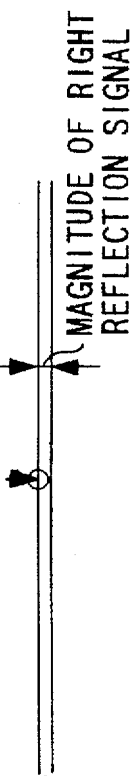

DRIVE SIGNAL OF LEFT TRANSMITTER

LEFT RECEIVER OUTPUT
d
e

TIMING PULSE
ts

LEFT DETECTION CIRCUIT OUTPUT

LEFT SAMPLE/HOLD CIRCUIT OUTPUT
0V
MAGNITUDE OF LEFT REFLECTION SIGNAL

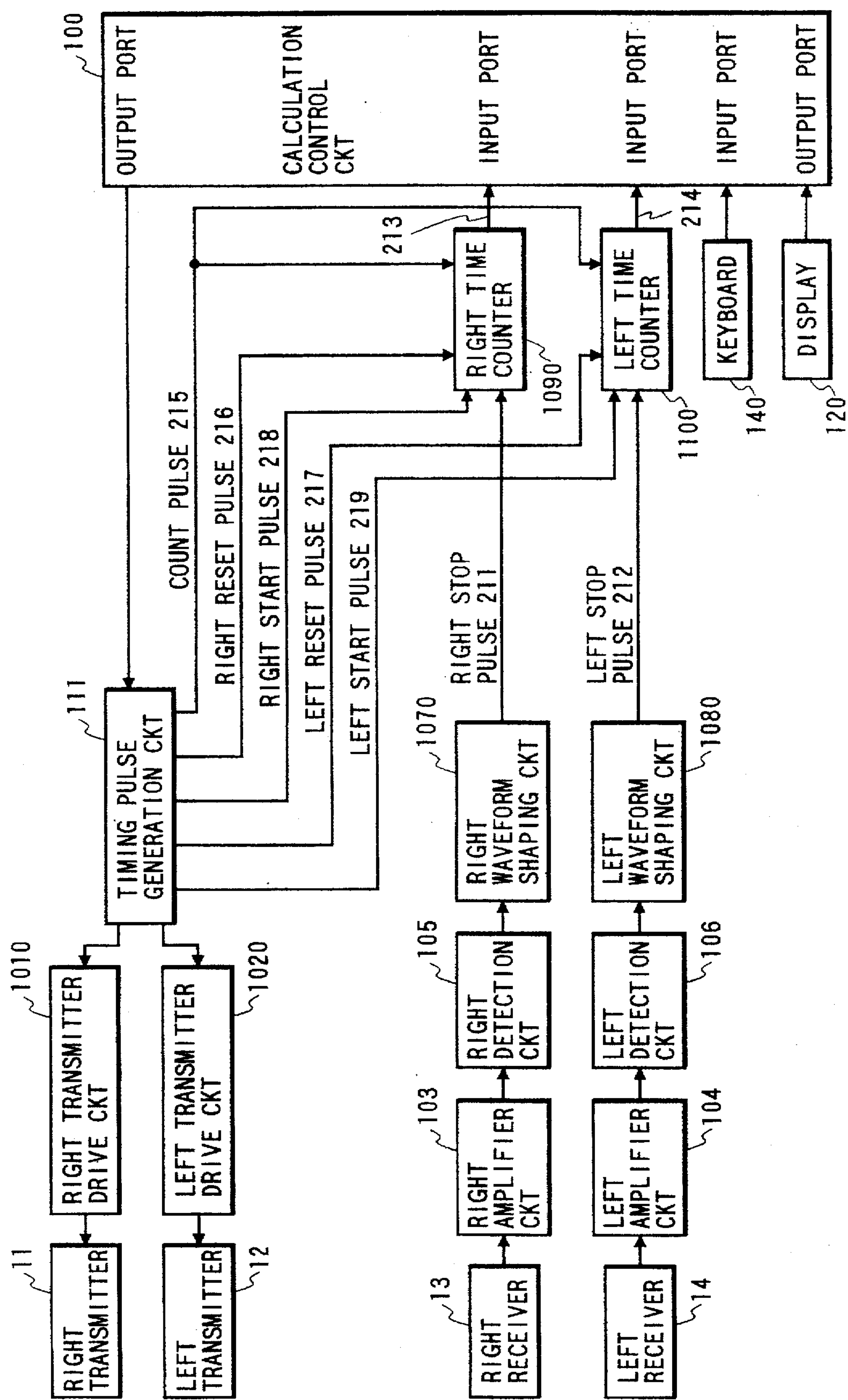
FIG. 11
OUTPUT PORT
CALCULATION CONTROL CKT
INPUT PORT
INPUT PORT
INPUT PORT
OUTPUT PORT
100
RIGHT TIME COUNTER
LEFT TIME COUNTER
KEYBOARD
DISPLAY
213
214
1090
1100
140
120
COUNT PULSE 215
RIGHT RESET PULSE 216
RIGHT START PULSE 218
LEFT RESET PULSE 217
LEFT START PULSE 219
RIGHT STOP PULSE 211
LEFT STOP PULSE 212
TIMING PULSE GENERATION CKT
111
RIGHT WAVEFORM SHAPING CKT
1070
LEFT WAVEFORM SHAPING CKT
1080
RIGHT TRANSMITTER DRIVE CKT
1010
LEFT TRANSMITTER DRIVE CKT
1020
RIGHT DETECTION CKT
105
LEFT DETECTION CKT
106
RIGHT AMPLIFIER CKT
103
LEFT AMPLIFIER CKT
104
RIGHT TRANSMITTER
11
LEFT TRANSMITTER
12
RIGHT RECEIVER
13
LEFT RECEIVER
14

EYE EXAMINATION APPARATUS USING ULTRASONIC WAVE RADIATION

BACKGROUND OF THE INVENTION

1. Field of the Invention

This invention relates to an eye examination apparatus for effecting the measurement of eye refractive power, the measurement of cornea shape, etc.

2. Related Background Art

Eye examination apparatuses for measuring eye refractive power, etc., in which a main mechanism includes a measuring unit placed on a slidable bed have heretofore been popular, and right and left eyes to be examined have been automatically judged by the position of the slidable bed.

Recently, however, apparatuses which are not provided with such a slidable bed (for example, apparatus of the portable type which can be freely carried by an examiner) have also appeared.

Accordingly, in an "eye examination apparatus" described, for example, in Japanese Patent Application Laid-Open No. 4-73046, there is proposed the right and left eye judging function of an eye examination apparatus which is not provided with a slidable bed. This eye examination apparatus is such that a light beam is applied to the sideways part of an eye to be examined and on the basis of the reflected light thereof, discrimination between right and left eyes is effected.

In this prior-art eye examination apparatus, however, the light beam applied to the sideways part of the eye to be examined affects a measuring light beam used for the measurement of the eye to be examined. If disturbance to the measuring light beam occurs, a reduction in measurement accuracy will result.

Also, the portable eye examination apparatus is convenient to carry and therefore is often used for examinations of a person lying down on a bed. In such cases, the eye examination apparatus becomes capable of being used from various directions relative to the examinee (for example, from sideways of and right above the examinee's face), but in such situations of use, discrimination between a right and left eye to be examined becomes impossible.

SUMMARY OF THE INVENTION

It is the object of the present invention to provide an eye examination apparatus which can exactly judge the right or left eye is to be examined.

The above object is achieved by an eye examination apparatus provided with an ultrasonic transmitter for transmitting ultrasonic wave radiation to an area around an eye to be examined, an ultrasonic receiver for receiving the reflected ultrasonic wave radiation and a judging device for judging whether the eye to be examined is the right eye or the left eye based on the result of the reception by the ultrasonic receiver.

The above object can also be achieved by an eye examination apparatus provided with a measuring device for measuring an eye to be examined, and a designating unit for designating whether the eye to be examined is the right eye or the left eye.

The above object is achieved by an eye examination apparatus provided with a measuring device for measuring an eye to be examined, a judging device for judging whether the eye to be examined is the right eye or the left eye, a designating unit for designating whether the eye to be examined is the right eye or the left eye, and a selecting device for selecting one of the judging device and the designating unit.

According to the present invention, the judgment of the right or left eye to be examined is done by the use of ultrasonic wave radiation and therefore, measuring light is not adversely affected. Accordingly, a highly accurate measurement result can be obtained. It is also possible to designate the right or left eye to be examined.

BRIEF DESCRIPTION OF THE DRAWINGS

FIG. 5 is a block diagram of an electric circuit in an embodiment of the eye examination apparatus according to the present invention.

FIGS. 8A to 8I are illustrations regarding the outputs of various signals in an embodiment of the eye examination apparatus according to the present invention.

FIG. 11 is a block diagram of an electric circuit in an embodiment of the eye examination apparatus according to the present invention.

DESCRIPTION OF THE PREFERRED EMBODIMENTS

An embodiment of the present invention when applied to an eye examination apparatus of the portable type will hereinafter be described with reference to the drawings.

Figure 1:
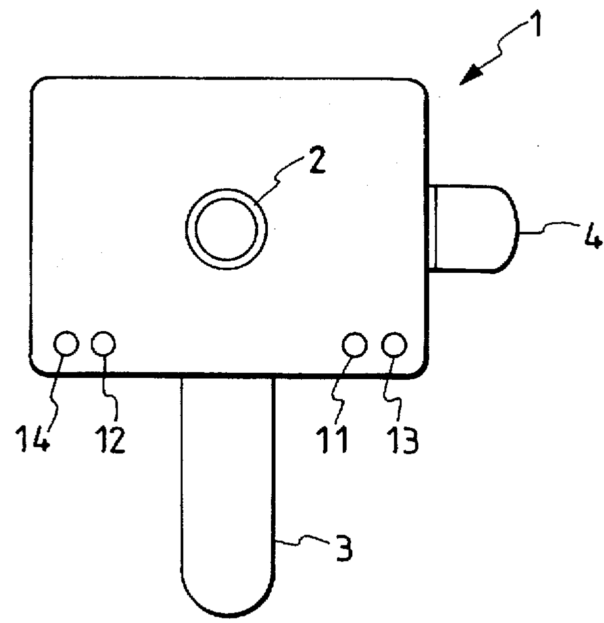
FIG. 1 is a front view of an embodiment of an eye examination apparatus according to the present invention.
Figure 2:
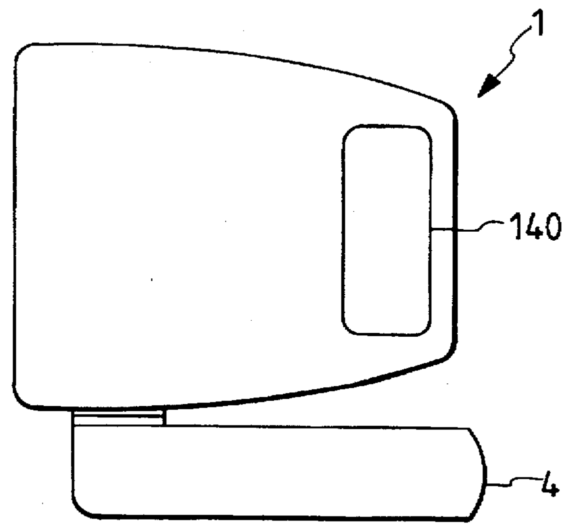
FIG. 2 is a top plan view of an embodiment of the eye examination apparatus according to the present invention.

FIGS. 1 and 2 show the external appearance of the eye examination apparatus according to the present embodiment. As shown in FIG. 1, there are provided in the front of the eye examination apparatus 1 a measuring window 2 transmitting measuring light therethrough and applying it to an eye to be examined (not shown) and introducing the reflected light thereof, a right transmitter 11 for transmitting ultrasonic wave radiation, a right receiver 13 for receiving the reflected wave radiation of the ultrasonic wave radiation, a left transmitter 12 for transmitting ultrasonic wave radiation, and a left receiver 14 for receiving the reflected wave radiation of the ultrasonic wave radiation. The transmitters are disposed at right and left about a straight line containing the optical axis of the measuring light at a level lower than the measuring window 2. The receivers are disposed adjacent to the corresponding transmitters. If the transmitters and receivers are thus disposed at locations separate from the measuring window 2, when eye examination is effected, these will not enter an examinee's field of view and will not bother the examinee. Of course, these transmitters and receivers may be disposed obliquely upwardly of the measuring window 2. Also, a grip 3 for handhold is provided on the underside of the eye examination apparatus 1.

Figure 6:
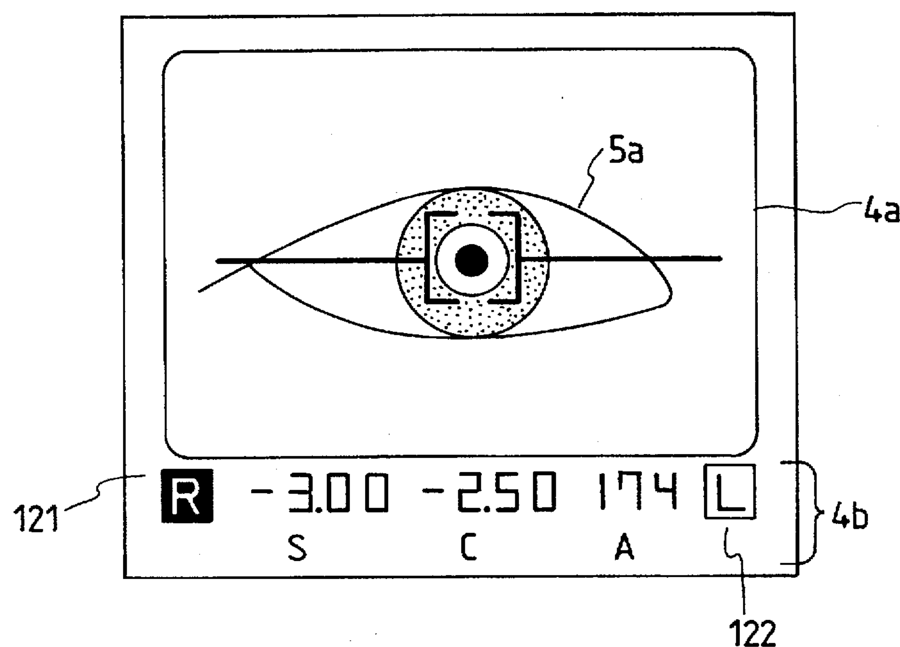
FIG. 6 is an illustration of a viewfinder in an embodiment of the eye examination apparatus according to the present invention.

On the upper surface of the eye examination apparatus 1, as shown in FIG. 2, there is installed a keyboard 140. Any information necessary to effect eye examination is inputted by the use of this keyboard 140. Also, a viewfinder 4 is mounted on a side of the eye examination apparatus 1. In the display area of the viewfinder 4, as shown in FIG. 6, there are present an area 4*a* in which the image of the eye to be examined (here the right eye 5*a*) is displayed, and an area 4*b* display-controlled by a display 120 (see FIG. 5).

Figure 3:
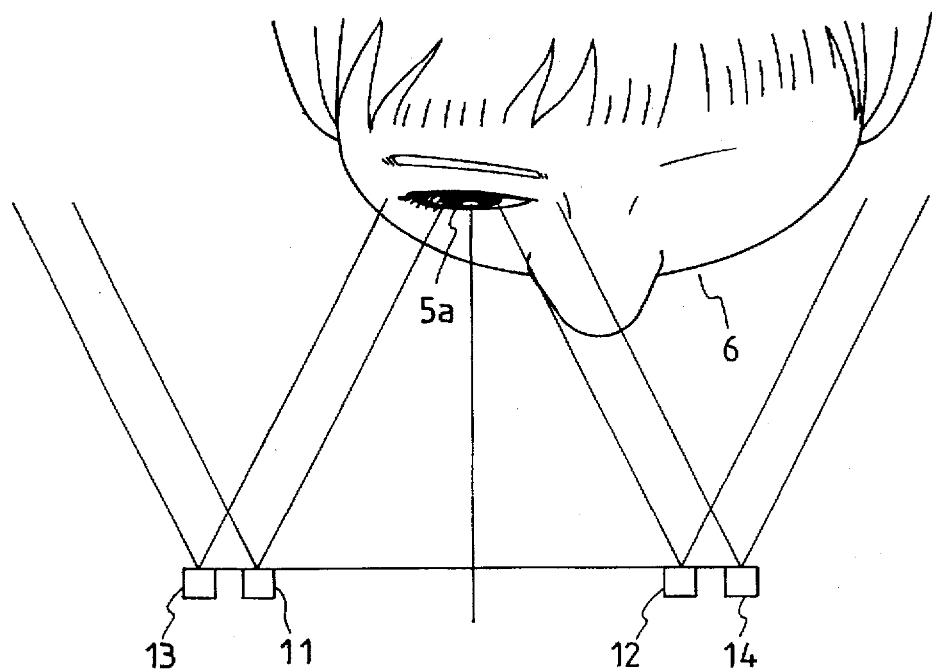
FIG. 3 is an illustration regarding the transmission and reception range of ultrasonic wave radiation (when seen from above) in an embodiment of the eye examination apparatus according to the present invention.
Figure 4:
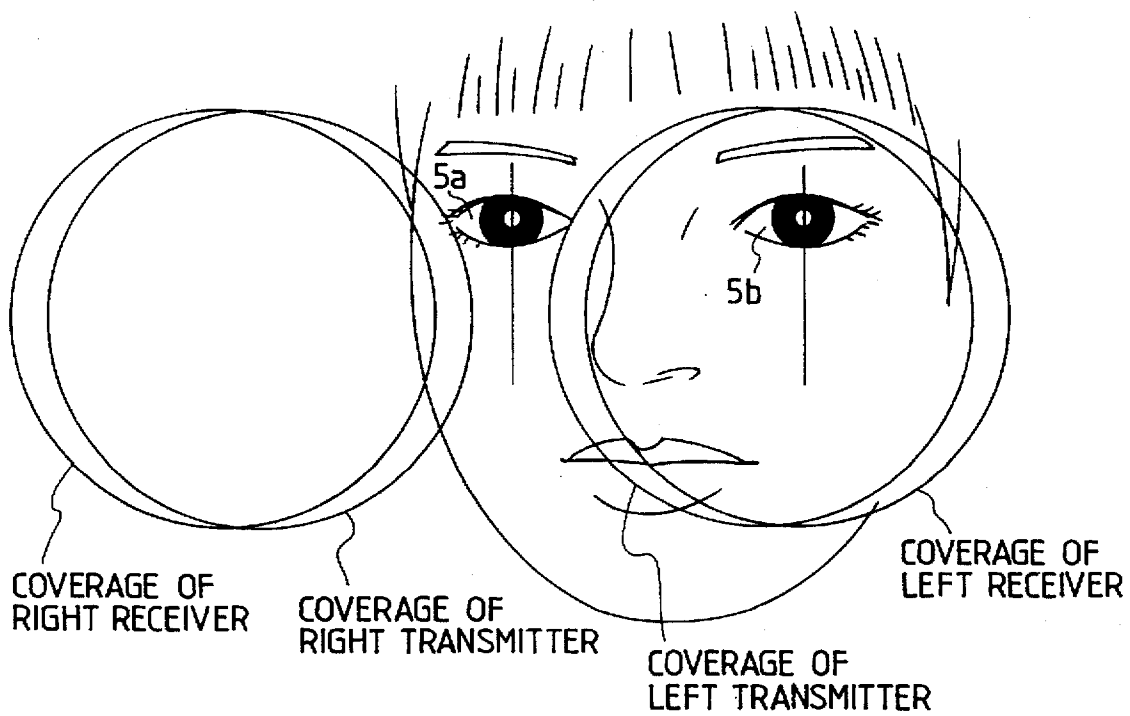
FIG. 4 is an illustration regarding the transmission and reception range of ultrasonic wave radiation (when seen from the front) in an embodiment of the eye examination apparatus according to the present invention.

FIGS. 3 and 4 show the radiation ranges of the ultrasonic waves outputted by the respective transmitters. In these figures, the examination of the right eye 5*a* of an examinee 6 is effected, and in this case, almost all of the ultrasonic wave transmitted from the left transmitter 12 is reflected by the face of the examinee 6. On the other hand, most of the ultrasonic wave transmitted from the right transmitter 11 passes the side of the face of the examinee 6. Thus, the left receiver 14 receives a stronger reflected signal than the right receiver 13. Of course, when the left eye 5*b* of the examinee 6 is examined, a phenomenon converse to this occurs. That is, if the intensities of the reflected waves received by the respective receivers are compared with each other when the measuring window 2 is opposed to the left eye 5*b*, whether the eye to be examined is the right eye or the left eye can be judged. The ultrasonic wave is very weak in the amount of reflection from hair and therefore, even in the case of an examinee having much hair on both sides of his or her face, accurate judgment can be performed.

Description will hereinafter be made of the judgment process to determine whether the right or left eye is examined by the eye examination apparatus of the present embodiment. Constituents necessary for this judgment process will first be described with reference to FIG. 5.

In the eye examination apparatus 1, there are provided a transmitter drive circuit 101 oscillating a predetermined frequency (e.g. about 40 KHz), a switching circuit 102 for selectively delivering a drive signal of said frequency to the right transmitter 11 or the left transmitter 12, and a timing pulse generation circuit 111 outputting a timing pulse to the switching circuit 102 in conformity with a given control signal. These are used during the transmission of the ultrasonic waves.

Also, as a receiving system for the ultrasonic waves, there are provided amplifier circuits (a right amplifier circuit 103 and a left amplifier circuit 104), detection circuits (a right detection circuit 105 and a left detection circuit 106), sample/hold circuits (a right sample/hold circuit 107 and a left sample/hold circuit 108), a multiplexer 109 and an A/D conversion circuit 110.

Each of the multiplexer 109, the A/D conversion circuit 110 and the timing pulse generation circuit 111 is connected to a calculation control circuit 100.

The calculation control circuit 100 has connected thereto the aforementioned keyboard 140, the display 120, a buzzer 130 and a communication circuit 150 for a printer. The communication circuit 150 for the printer can output information given from the calculation control circuit 100 toward a printer (not shown) provided discretely from the eye examination apparatus 1 by radio (in the present embodiment, infrared radiation). The calculation control circuit 100 is comprised of a CPU and a memory storing therein a program executed by the CPU.

Figure 7:
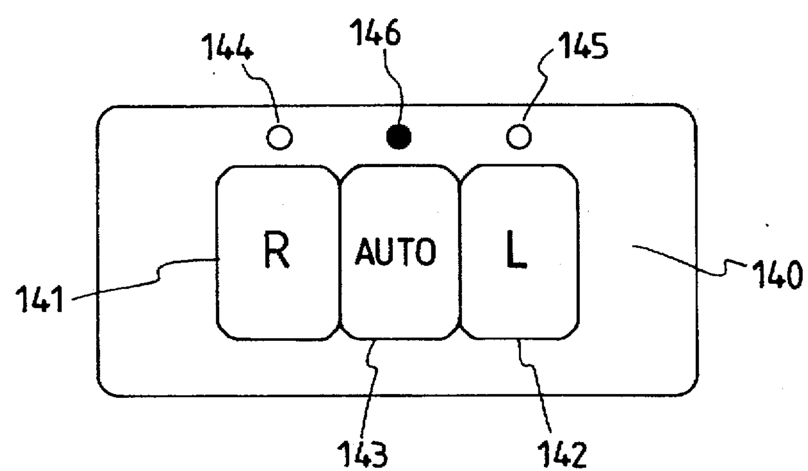
FIG. 7 is an illustration of a keyboard in an embodiment of the eye examination apparatus according to the present invention.
Figures 9A, 9B, 9C, 9D, 9E:
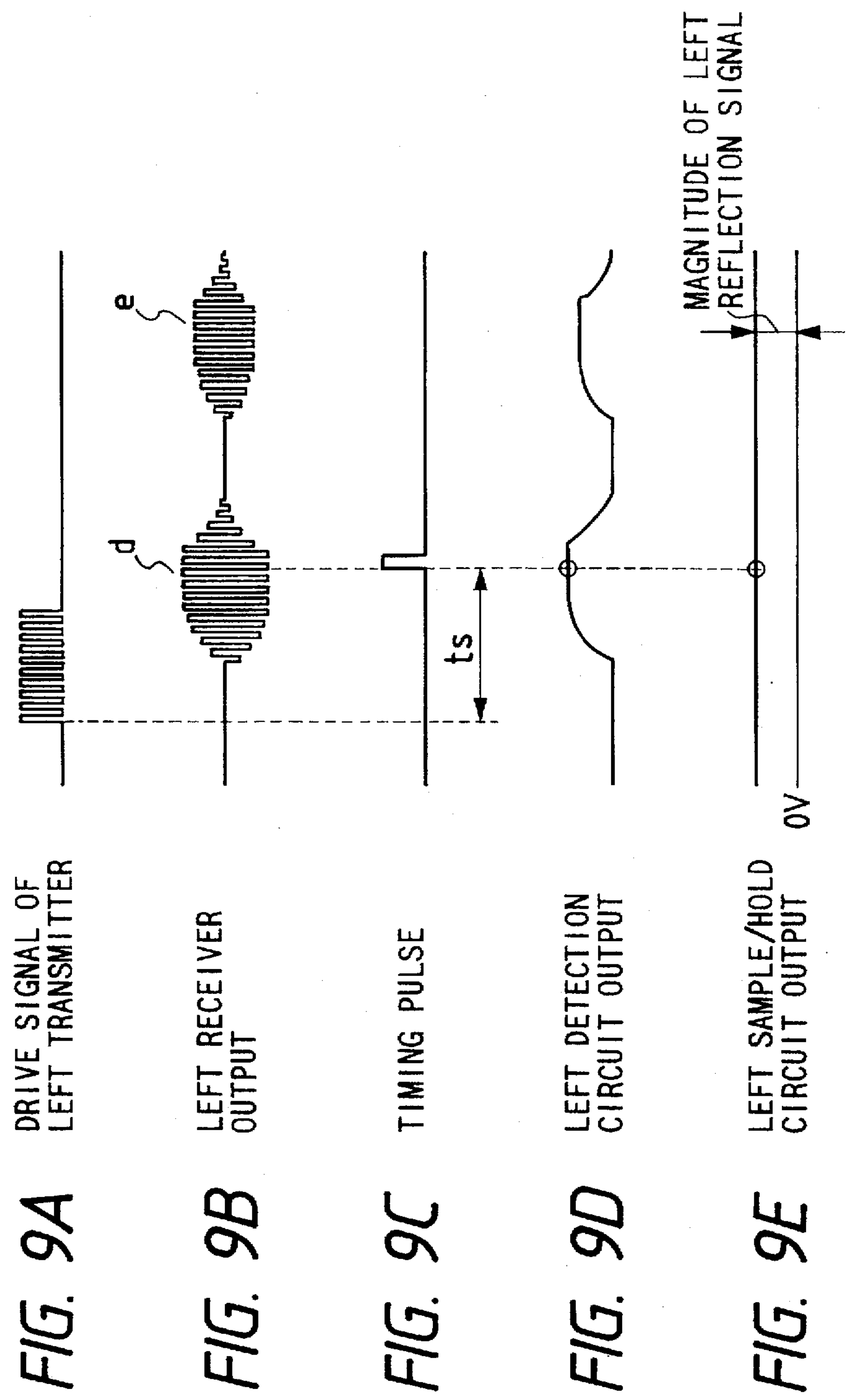
FIGS. 9A to 9E are illustrations regarding the outputs of various signals in an embodiment of the eye examination apparatus according to the present invention.

The details of the keyboard 140 are shown in FIG. 7. As shown in FIG. 7, on the central portion to determine the keyboard, there is provided a right-left auto-key 143 for rendering the judgment process to determine the right or left eye executable. A right measurement key 141 and a left measurement key 142 are disposed on the opposite sides of the right-left auto-key 143. The respective keys are provided with lamps (an auto-measurement lamp 146, a right measurement lamp 144 and a left measurement lamp 145) adapted to be turned on or off in conformity with the set contents thereof. On the other hand, a right measurement lamp 121 for effecting display equal to that by the right measurement lamp 144 and a left measurement lamp 122 for effecting display equal to that by the left measurement lamp 145 are provided on the display area 4*b* (see FIG. 6) in the viewfinder.

The procedure of the process of judging the right and left eyes will now be described with the flow of the eye examining work. It is to be understood here that the right-left auto-key 143 has been pre-depressed on the keyboard 140. With this, the auto-measurement lamp 146 is in its turned-on state.

An examiner first closes a measurement starting switch (not shown) to thereby render the eye examination apparatus 1 capable of effecting measurement. Thus, measuring light comes to be continuously applied from the measuring window 2. Thereafter, the examiner 2 positions the measuring window 2 forwardly of an eye to be examined (here, the right eye 5*a*) and effects the alignment between the optical axes of the eye to be examined and the eye examination apparatus side while looking into the viewfinder 4.

On the other hand, the calculation control circuit 100 detects the closing operation of the measurement starting switch and outputs a control signal to the timing pulse generation circuit 111. In response to it, the timing pulse generation circuit 111 transmits a timing pulse conforming to the control signal to the switching circuit 102. A drive signal as shown in FIG. 8A is being outputted from the transmitter drive circuit 101, and the switching circuit 102 delivers this drive signal alternately to the right transmitter 11 and the left transmitter 12 in accordance with the given timing pulse. If the transmitters are thus driven alternately, the interference between the ultrasonic waves can be prevented.

The manner in which the drive signal is delivered to the respective transmitters is shown in FIGS. 8B and 8C. FIG. 8B shows the drive signal given to the left transmitter 12, and FIG. 8C shows the drive signal given to the right transmitter 11. Each transmitter transmits ultrasonic wave radiation as long as it is given the drive signal. When the examinee's right eye is being examined, the left receiver 14 receives the ultrasonic wave radiation reflected by the examinee's face and outputs a detection signal as shown, for example, in FIG. 8D. On the other hand, the right receiver 13 receives the ultrasonic wave radiation reflected only by a part of the examinee's face and outputs a detection signal as shown in FIG. 8E.

The transmission of the ultrasonic wave radiation by each transmitter is effected waiting for the reception by the other receiver. For example, when the ultrasonic wave radiation has been transmitted from the left transmitter 12 (a in FIG. 8B), the transmission of the ultrasonic wave radiation by the right transmitter 11 is effected, (c in FIG. 8C) after the reflected wave of the ultrasonic wave radiation from the left transmitter has been received by the left receiver 14 (b in FIG. 8D). If each transmitter is thus driven, the right and left transmitted waves and received waves of the ultrasonic waves will not interfere with each other.

The detection signal outputted from the left receiver 14 is amplified by the left amplifier 104, whereafter it is converted into a signal of such a waveform as shown in FIG. 8F by the left detection circuit 106. The left sample/hold circuit 108 samples this signal and outputs the value thereof. This output is shown in FIG. 8H. The sampling operation of the left sample/hold circuit 108 is performed in accordance with the timing pulse sent from the timing pulse generation circuit 111.

As shown in FIGS. 9A to 9E, this timing pulse is sent when a time ts has elapsed after a point of time at which the left transmitter drive signal (FIG. 9A) has been outputted, and the length of the time ts is set with the time required for the reflected wave radiation reflected by the examinee's face to arrive at the receiver taken into account.

If this is done, the judgment of the right or left eye is effected based on the result of the reception at the point of time whereat the time ts has elapsed and therefore, an accurate judgment result can be obtained. Specifically, it becomes possible to detect only the reflected wave radiation from the examinee's face, and the judgment of the right or left eye which is free of the influence of the reflected wave radiation from an object at a predetermined or greater distance from the eye examination apparatus can be carried out.

Accordingly, it becomes possible to detect only the reflected wave radiation (d in FIG. 9B) from the examinee's face, and the influence (e in FIG. 9B) of the reflected wave radiation from the object at the predetermined or greater distance from the eye examination apparatus can be prevented. Specifically, when the eye of an examinee lying down is examined, the influence of the reflected wave radiation from an object (for example, a bed) located at a position separate from the examinee's face can be prevented.

When use is made of a medium for transmission and reception which is high in propagation speed (specifically, a light beam), the setting of the aforementioned time ts is difficult, but if as in the present embodiment, use is made of ultrasonic wave radiation which is relatively low in propagation speed, the setting of the time ts can be realized easily.

Also, even when the examination of the eyes of a plurality of examinees is effected, the distance between the eye examination apparatus and the examinee's faces is usually constant and therefore, there will be no particular problem even if the length of the time ts is preset.

On the other hand, the detection signal outputted from the right receiver 13 is converted into a signal as shown in FIG. 8G by the right amplifier 103 and the right detection circuit 105, whereafter it is outputted from the right sample/hold circuit 107, as shown in FIG. 8I. The sampling operation of the right sample/hold circuit 107, as previously described, is performed in accordance with the timing pulse sent from the timing pulse generation circuit 111. With respect also to this timing pulse, the setting of the time ts is done as previously described.

The multiplexer 109 receives the output of the right sample/hold circuit 107 and the output of the left sample/hold circuit 108, and outputs them alternately to the A/D conversion circuit 110. That is, the multiplexer 109 outputs to the A/D conversion circuit 110 the signal switched at any timing by the calculation control circuit 100 and held in the right sample/hold circuit 107 or the signal held in the left sample/hold circuit 108, in conformity with the aforementioned timing. As this switching timing, the timing at which the first signal is converted by the A/D conversion circuit 110 and delivered to the calculation control circuit 110 and immediately thereafter, the next signal is outputted to the A/D conversion circuit 110 is preferable.

The A/D conversion circuit 110 converts the given signal (analog signal) into a digital signal and delivers it to the calculation control circuit 100. This calculation control circuit 100 effects the following judgment on the basis of this signal. The judgment may be effected, for example, at a frequency of 1 to 10 times per second.

(1) When $IR>IL\times K$, the eye to be examined is judged to be the left eye.

(2) When $IL>IR\times K$, the eye to be examined is judged to be the right eye.

(3) When $IR\leqq IL\times K$ and $IL\leqq IR\times K$, the judgment is impossible.

Here,

IR: the magnitude of the output of the right sample/hold circuit 107 (FIG. 8I)

IL: the magnitude of the output of the left sample/hold circuit 108 (FIG. 8H)

K: a constant greater than 1 and desirably the order of 1.5 to 5.

As shown in items (1) to (3) above, the judgment of the right or left eye is effected based on the relative intensity of the ultrasonic wave received by each receiver. When for example, the eye to be examined is judged to be the right eye by the calculation control circuit 100, the right measurement lamp 121 in the viewfinder is turned on. When conversely, the eye to be examined is judged to be the left eye, the left measurement lamp 122 is turned on. When the alignment between the optical axes of the eye to be examined and the eye examination apparatus side is being effected, the judgment often fluctuates. Accordingly, in the present embodiment, when the right or the left eye has been once judged, the display by the measurement lamp is adapted to be fixed until the next judgment is done.

When the optical axis of the eye to be examined and the optical axis of the eye examination apparatus side coincide with each other, a measuring circuit (not shown) provided in the eye examination apparatus executes the automatic introduction of the measuring light reflected by the eye to be examined. The introduced measuring light is converted into an electrical signal by the measuring circuit and is outputted to the calculation control circuit 100. The calculation control circuit 100 effects a predetermined calculation based on this signal, and displays the result of the calculation (for example, the spherical degree of the eye to be examined) within the viewfinder through the display 120. Also when the automatic introduction is being effected, the process of judging the right or the left eye is carried out as occasion calls, and the result of the aforementioned calculation is stored in a memory in the calculation control circuit 100 with the result of the judgments of the right and left eyes. The stored data can be outputted later from a printer.

Also, when the judgment of item (3) above is done immediately before the automatic introduction is effected or while the automatic introduction is being effected, the measurement lamps (the right measurement lamp 121 and the left measurement lamp 122) in the viewfinder and the measurement lamps (the right measurement lamp 144 and the left measurement lamp 145) on the keyboard 140 are turned on and off. The examiner can recognize by such turn-on-and-off display that the right and left eyes have not been decided in the aforedescribed judging process. The buzzer 130 may be made to sound with the turn-on-and-off display.

When there is such an alarm output, the examiner can depress the right measurement key 141 or the left measurement key 142 (here the right measurement key 141 because this is the examination of the right eye). The calculation control circuit 100 detects it and decides upon the right or the left eye regarding the result of the calculation in which the automatic judgment of the right or the left eye has not been done.

Now, the eye examination apparatus 1, which is of the portable type, may be used in various situations. For example, one of those situations is a case where the eyes of an examinee lying down on a bed are examined. In such a case, the eye examination apparatus 1 is not always disposed in a correct direction (a direction as shown in FIGS. 3 and 4) relative to the examinee's face, but eye examination is sometimes effected from sideways of or right above the examinee's face. When the eye examination apparatus 1 and the examinee's face assume such positional relationship, the aforedescribed automatic judgment of the right or the left eye becomes meaningless.

Accordingly, in such a case, the examiner depresses the right measurement key 141 or the left measurement key 142 in conformity with the right or left eye to be examined before he effects the examination. One of the measurement lamps on the keyboard 140 which corresponds to the depressed key is turned on. The calculation control circuit 100 judges the eye to be examined to be the right eye when it detects the depression of the right measurement key 141, and judges the eye to be examined to be the left eye when it detects the depression of the left measurement key 142. The calculation control circuit 100 stops the transmission of the ultrasonic wave radiation by each transmitter through the switching circuit 102 when one of the right measurement key 141 and the left measurement key 142 is depressed.

On the other hand, the result of the judgment by the calculation control circuit 100 is reflected in the measurement lamp in the viewfinder and also is stored in the memory concomitantly with measurement data calculated in the eye examination thereafter.

If the right or left eye to be examined can thus be designated by manual inputting, various situations of use can be coped with flexibly. During manual inputting, the ultrasonic wave is not transmitted and therefore, examination can also be carried out on an animal disliking the ultrasonic wave.

While in the present embodiment, the intensities of the reflected waves received by the respective receivers are compared with each other to thereby judge whether the eye to be examined is the right eye or the left eye, this is not restrictive, but the judgment may be done based on the time difference between the ultrasonic waves received by the respective receivers.

Figure 10A:
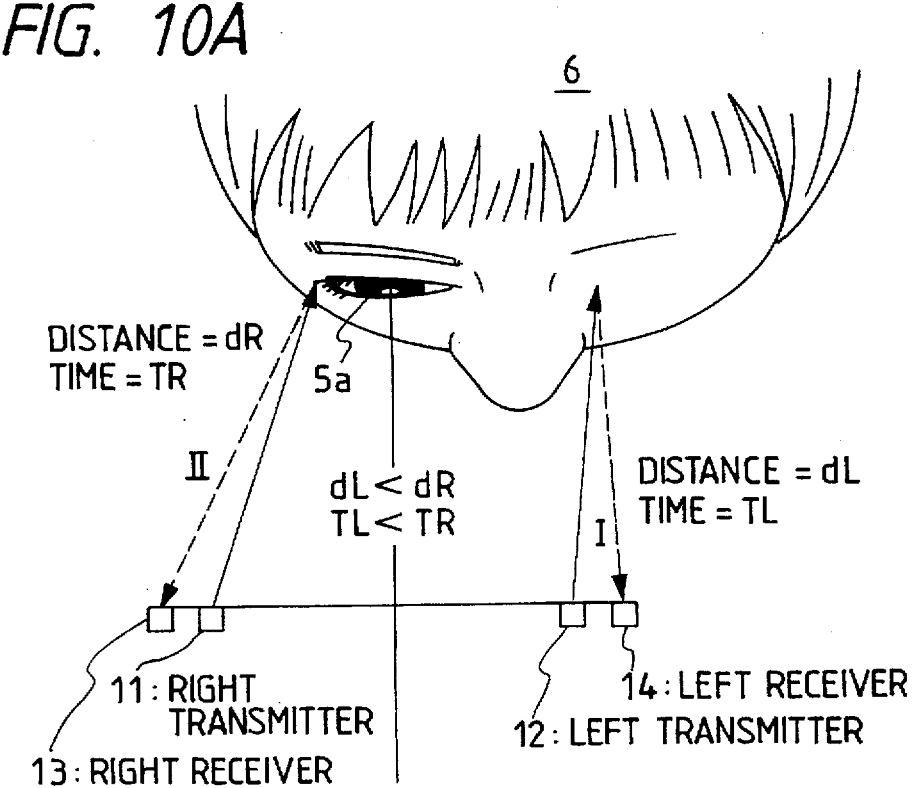
FIGS. 10A and 10B are illustrations regarding the transmission and reception route of the ultrasonic wave radiation (when seen from above) in an embodiment of the eye examination apparatus according to the present invention.

When for example, the right eye has been examined, as shown in FIG. 10A, the ultrasonic wave radiation transmitted from the left transmitter 12 passes along a route I and is reflected by the examinee's face, and arrives at the left receiver 14. Also, the ultrasonic wave radiation transmitted from the right transmitter 11 passes along a route II and is reflected by the examinee's face, and arrives at the right receiver 13.

In this case, as shown in FIG. 10A, the distance dL of the route I is shorter than the distance dR of the route II and therefore, the required time TL for the former becomes shorter than the required time TR for the latter.

Figure 10B:
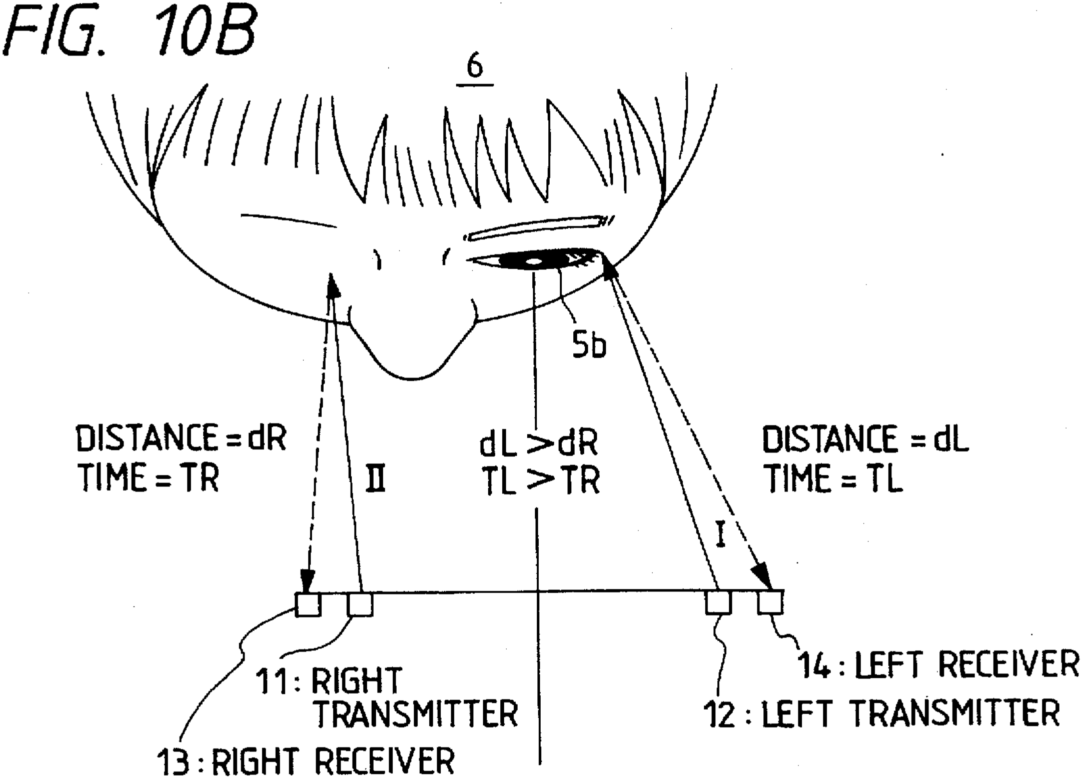

Conversely, when the left eye has been examined, as shown in FIG. 10B, the distance dL of the route I is longer than the distance dR of the route II and therefore, the required time TL for the former becomes longer than the required time TR for the latter.

If by the utilization of the above-described phenomena, the time TL and the time TR are compared with each other, discrimination between the right or the left eye can be accomplished.

Such discrimination between the right or the left eye can be realized, for example, by the use of the construction of FIG. 11. Constituents in FIG. 11 which are the same as those in FIG. 5 are given the same reference numerals and need not be described.

The timing pulse generation circuit 111 first outputs a right reset pulse 216 and resets a right time counter 1090 to zero. Subsequently, the timing pulse generation circuit 111 drives a right transmitter drive circuit 1010 and causes ultrasonic wave radiation to be transmitted from the right transmitter 11 and also, sends a right start pulse 218 to the right time counter 1090. After having received this pulse, the right time counter 1090 starts counting based on a counter pulse 215 sent from the timing pulse generation circuit 111.

The ultrasonic wave radiation reflected by the examinee's face arrives at the right receiver 13 and is inputted as a right stop pulse 211 to the right time counter 1090 via the right amplifier circuit 103, the right detection circuit 105 and a right waveform shaping circuit 1070. In response to the right stop pulse 211, the right time counter 1090 stops counting. Thereby, the result of counting corresponding to the time TR from after the ultrasonic wave radiation has been transmitted from the right transmitter 11 until it is received by the right receiver 13 is stored in the right time counter 1090.

When the measurement of the right eye side is thus completed, the measurement of the left eye side is executed.

Specifically, the timing pulse generation circuit 111 first outputs a left reset pulse 217 and resets a left time counter 1100 to zero. Subsequently, the timing pulse generation circuit 111 drives a left transmitter drive circuit 1020 and causes ultrasonic wave radiation to be transmitted from the left transmitter 12 and also, sends a left start pulse 219 to the left time counter 1100. After having received this pulse, the left time counter 1100 starts counting based on the counter pulse 215 sent from the timing pulse generation circuit 111.

The ultrasonic wave radiation reflected by the examinee's face arrives at the left transmitter 14 and is inputted as a left stop pulse 212 to the left time counter 1100 via the left amplifier circuit 104, the left detection circuit 106 and a left waveform shaping circuit 1080. In response to the left stop pulse 212, the left time counter 1100 stops counting. Thereby, the result of counting corresponding to the time TL from after the ultrasonic wave radiation has been transmitted from the left transmitter 12 until it is received by the left receiver 14 is stored in the left time counter 1100.

Thereafter, the calculation control circuit 100 reads out the result of the counting by the right time counter 1090 as a signal 213, and the result of the counting by the left time counter 1100 as a signal 214, and effects the aforedescribed judging process to thereby discriminate between the right or the left eye. The result of this is displayed on the display 120.

What has been described above is the embodiment of the present invention, but when the eye examination apparatus is provided with only one transmitter or one receiver (for example, the right transmitter 11 and the right receiver 13), if the result of the reception by the right receiver 13 is compared with the intensity of a predetermined reflected wave, the judgment of the right or left eye will become possible.

What is claimed is:

1. An eye examination apparatus, comprising:

an ultrasonic transmitter for transmitting ultrasonic wave radiation to an area around an eye to be examined;

an ultrasonic receiver for receiving reflected radiation of said ultrasonic wave radiation; and a judging device for judging whether said eye to be examined is the right eye or the left eye based on the reflected radiation received by said ultrasonic receiver, wherein said ultrasonic transmitter has at least two transmitting portions for transmitting said ultrasonic wave radiation, and a drive circuit for driving said transmitting portions alternately.

2. An eye examination apparatus according to claim 1, provided with a detector for detecting that a predetermined time has elapsed from a point of time at which said one of transmitting portions has transmitted said ultrasonic wave radiation, and a holding circuit for holding a signal corresponding to the reflected radiation being received by said ultrasonic receiver at a point of time whereat said predetermined time has elapsed, said judging device judging whether said eye to be examined is the right eye or the left eye based on the signal held by said holding circuit.

3. An eye examination apparatus comprising:

a measuring device for measuring an eye to be examined;

a judging device for judging whether said eye to be examined is a right eye or a left eye;

a designating unit for an operator to designate whether said eye to be examined is a right eye or a left eye; and a selector for selecting one of said judging device and said designating unit.

4. An eye examination apparatus according to claim 3, wherein said judging device has an ultrasonic transmitter for transmitting ultrasonic wave radiation to an area around the eye to be examined, an ultrasonic receiver for receiving reflected radiation of said ultrasonic wave radiation, a judging circuit for judging whether said eye to be examined is the right eye or the left eye based on the reflected radiation received by said ultrasonic receiver, and a controller for stopping the transmission of said ultrasonic wave radiation from said ultrasonic transmitter when said designating unit is selected by said selector.

* * * * *